United States Patent [19]
Clark et al.

[11] Patent Number: 5,248,306
[45] Date of Patent: Sep. 28, 1993

[54] AXIAL RETAINER FOR FLOW CONNECTORS

[75] Inventors: John C. Clark, Zion; William J. Hook, Gurnee; Mark E. Larkin, Lindenhurst, all of Ill.

[73] Assignee: Abbott Laboratories, Abbott Park, Ill.

[21] Appl. No.: 934,996

[22] Filed: Aug. 25, 1992

[51] Int. Cl.⁵ .............................................. A61M 25/00
[52] U.S. Cl. ................................ 604/283; 604/905; 285/88; 285/320
[58] Field of Search ............... 604/174, 177, 178, 179, 604/282, 283, 905; 128/DIG. 26; 285/80-82, 87, 88, 114, 308, 320, 423

[56] References Cited

U.S. PATENT DOCUMENTS

| | | | |
|---|---|---|---|
| 1,209,374 | 12/1916 | Andreolli | 285/88 |
| 1,310,627 | 7/1919 | McEvilly | 285/114 |
| 1,458,337 | 6/1923 | Grier | 285/88 |
| 2,509,925 | 5/1950 | Ison | 285/87 |
| 3,469,864 | 9/1969 | Guerrero | 285/308 |
| 4,068,870 | 1/1978 | Whitney et al. | 285/320 |
| 4,230,109 | 10/1980 | Geiss | 285/114 X |
| 4,539,003 | 9/1985 | Tucker | 604/93 |
| 4,623,172 | 11/1986 | Shepheard | 285/309 |
| 4,631,056 | 12/1986 | Dye | 604/111 |
| 4,641,646 | 2/1987 | Schultz et al. | 604/283 X |
| 4,792,163 | 12/1988 | Kulle | 285/88 |
| 4,826,486 | 5/1989 | Palsrok et al. | 604/174 |
| 4,834,706 | 5/1989 | Beck et al. | 604/111 |
| 4,997,421 | 3/1991 | Palsrok et al. | 604/174 |
| 5,037,405 | 8/1991 | Crosby | 604/283 |

Primary Examiner—C. Fred Rosenbaum
Assistant Examiner—Corrine Maglione
Attorney, Agent, or Firm—A. Nicholas Trausch

[57] ABSTRACT

A retainer is used in combination with two tubular flow connectors to prevent the inadvertent disconnection of I.V. tubing sets. The retainer includes at least one open collar having a flexible opening so as to be radially and securely attachable adjacent to an increased diameter portion on a tubing connector. A pair of parallel straps connects the collar with an axially pivotable joint so as to facilitates easy manipulation and engagement of the retainer.

4 Claims, 4 Drawing Sheets

AXIAL RETAINER FOR FLOW CONNECTORS

BACKGROUND OF THE INVENTION

The present invention relates to a retainer for a fluid connector system used to transfer fluids from one flow conduit to a second flow conduit. More particularly, the invention relates to an axial retaining device used to prevent the inadvertent disengagement of tubing sets used in intravenous therapy.

Intravenous therapy involves the flow of a therapeutic solution from a sterile container to a catheter or needle positioned in a patient's vein. One or more sterile tubing sets are required to transfer the fluid from the container to the vein access device. Sterile connections with the tubing set can be made in a variety ways. For example, connections can be made using conventional male and female luer connectors. Also, connections can be made using sharp needle connectors with resealable elastomeric septums. Recently, due to the concerns about accidental needle sticks, blunt cannula connectors have been utilized to connect with prepierced elastomeric septums for intravenous fluid tubing sets.

A primary concern with any medical tubing connector is the inadvertent disengagement of the tubing sets. An uninterrupted flow of solution to the patient is important in intravenous therapy. Also, the sterility and integrity of the flow system must be maintained. Contaminants may be introduced into the flow system if the connectors are inadvertently disengaged and have to be reconnected.

The above concerns have led to medical guidelines and procedures that require that I.V. connections be secured together. A variety of securing mechanisms have been produced for securing I.V. connections. However, the known securing mechanisms are undesirable, for example, because of their size, complexity and/or expense, the discomfort they cause the patient, the amount of time and manipulation require from the healthcare provider to attach and release the securing mechanisms, or their lack of effectiveness in preventing disconnections.

Tape has been used when no suitable securing mechanism is available. However, tape has an inherent drawback when the connectors need to be disconnected. Also, tape is awkward to use when one of the connectors is in close proximity to the patient's body such as at the vein access site. Any movement of the connector at the vein access site can cause patient discomfort or damage to the vein wall.

Thus, there is a need for a simple and inexpensive retaining device that can prevent inadvertent disengagement of tubing sets. It is desirable that the retaining mechanism be readily engagable and disengagable. Further, it is desirable that the retaining mechanism be easy to manipulate, especially with I.V. tubing connectors used in close proximity to the patient's body and specifically to the vein access site.

SUMMARY OF THE INVENTION

Therefore it is a primary object of this invention to provide a simple and reliable construction for a retaining device used in combination with intravenous fluid flow connectors.

It is another object of this invention to provide an axial retaining mechanism for intravenous tubing connectors usable with a variety of connectors, such as sharp needles and resealable septums, blunt cannula and prepierced septums, and male and female luer connectors.

It is a further object of this invention to provide a retainer that is easy to manipulate by the healthcare provider, yet reliable in securing the connectors of the intravenous tubing set.

In accordance with these objectives, a retainer that is used in combination with first and second tubular flow connectors includes a first open collar having a flexible opening so as to be radially and securely attachable to the first tubular connector adjacent to an increased diameter radial shoulder. A second open collar has a second flexible opening so as to be radially and securely attachable to the second tubular connector adjacent to another increased diameter radial shoulder. A pair of parallel straps connects the first collar to the second collar. The straps are connected to the first and second collars by pairs of axially pivotable joints which facilitates easy manipulation of the retainer.

In an alternative embodiment, an integral connector and retainer is integrally manufactured with one of the flow connectors. A single open collar is pivotably connected by parallel straps to the integral connector and retainer and allows the second connector to be axially secured to the integral connector and retainer.

Other features and advantages of the present invention will become readily apparent from the following detailed description, the accompanying drawings, and the appended claims.

DESCRIPTION OF THE PREFERRED EMBODIMENT

Figure 1:
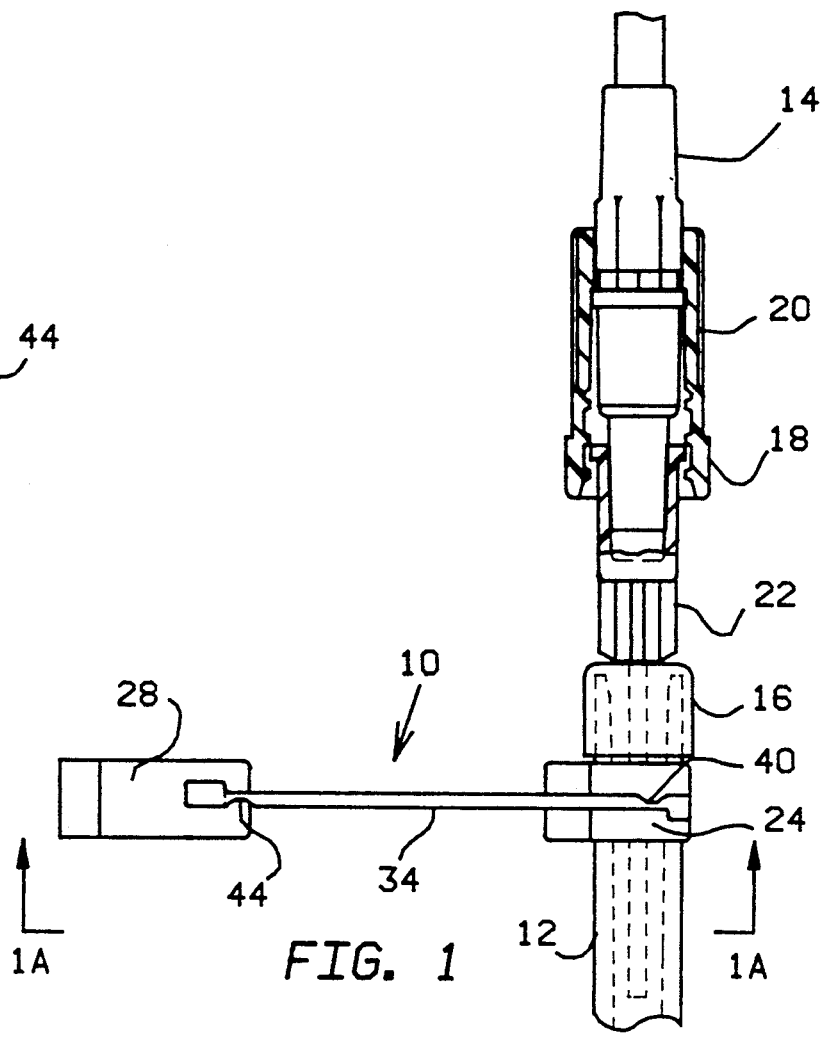
FIG. 1 is a partial cutaway side view of two flow connectors in fluid flow communication with a discrete retainer according to the present invention initially secured to one connector.

Referring to FIG. 1, a discrete retaining device 10 is shown in combination with a first intravenous tubing set connector 12 and a second intravenous tubing set connector 14. The first tubular connector includes an increased diameter radial shoulder 16. For example, such a shoulder may be the lip of the roll-over-reseal on the LifeShield ™ Prepierced Reseal sold by Abbott Laboratories. Alternatively the shoulder may be any increased diameter radial portion on the tubing connector near the end of the connector. A second increased diameter radial shoulder 18 is associated with the second tubular flow connector 14. As shown in FIG. 1, the tubular connector may include, for example, a luer lock 20 which includes an increased diameter portion. The luer lock secures a cannula device 22 to the second set. As shown in FIG. 1, the cannula is a LifeShield ™ Blunt Cannula sold by Abbott Laboratories and provides fluid flow connection with the prepierced reseal.

The retainer is preferably molded of a suitable flexible plastic such as polyvinyl chloride or other medical grade flexible material suitable for sterilization with the intravenous tubing set.

Figure 1A:
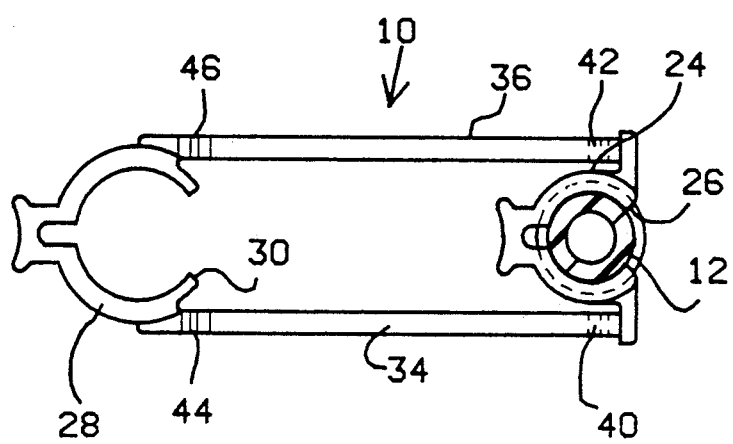
FIG. 1A is a bottom view of FIG. 1.

The retainer 10 as best seen in FIG. 1A includes a first open collar 24 forming a partial circle. The open collar has a first flexible opening 26 that is dimensioned so as to be radially attachable by a snap fit to the first tubular connector 12 adjacent to the first radial shoulder 16. The retainer 10 also includes a second open collar 28 having a second flexible opening 30 that is dimensioned to be radially attachable by a snap fit to the second tubular connector. A pair of parallel straps 34 and 36 connect the first collar 24 to the second collar 28. The straps are connected at a first end to the first collar by a first pair of axially pivotable joints 40 and 42. The straps are connected at the second end to the second collar by a second pair of axially pivotable joints 44 and 46.

Figure 3:
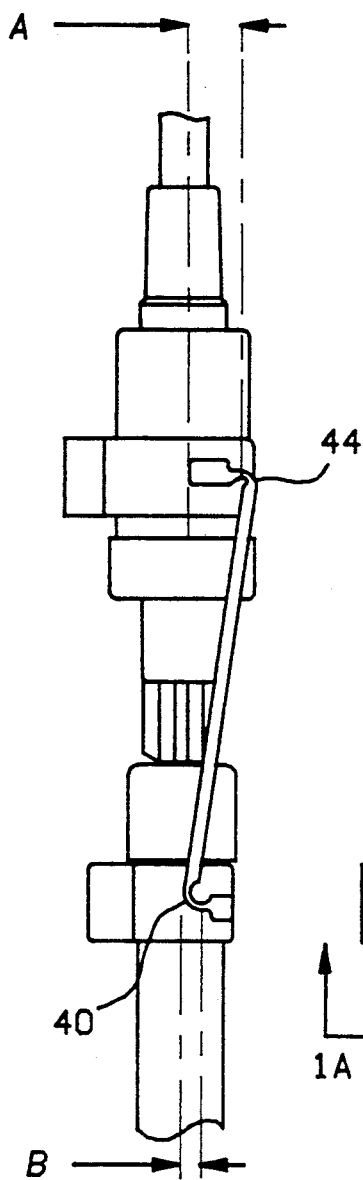
FIG. 3 is a side view of the retainer fully secured to both connectors.
Figure 2:
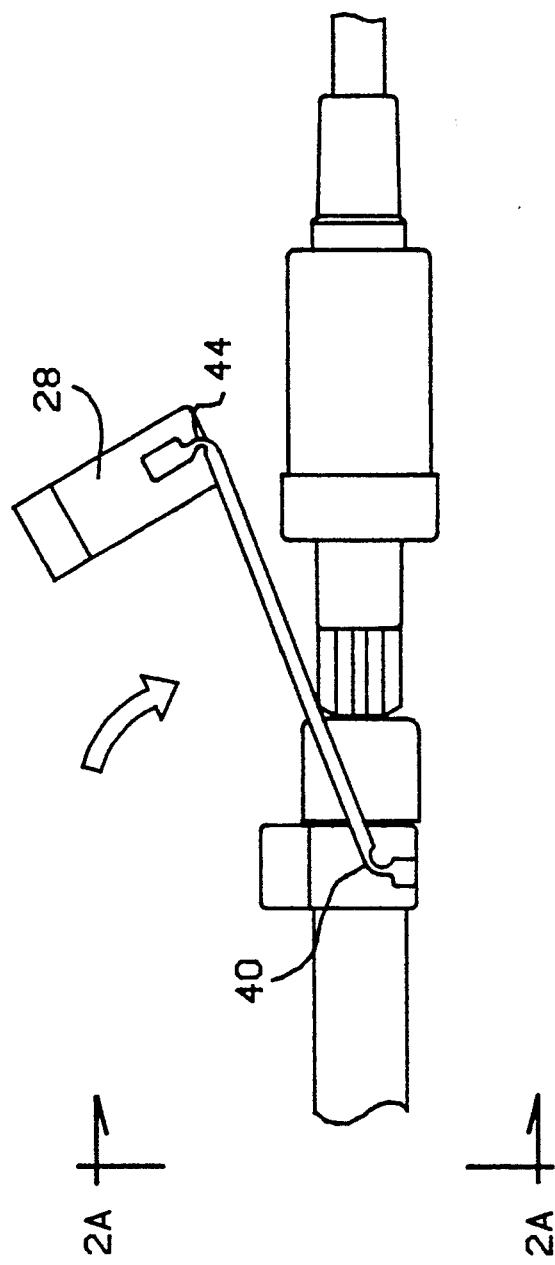
FIG. 2 is a side view of the retainer in an intermediate position prior to being fully secured to the second connector.
Figure 2A:
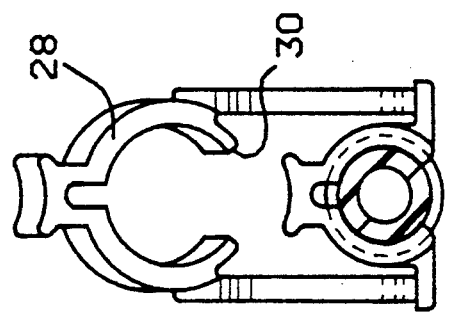
FIG. 2A is a bottom view of FIG. 2.

As best seen in FIG. 3, the first and second pairs of pivotable joints pivot in opposite axial directions. As shown, first joints 40 and 42 pivot axially up and second joints 44 and 46 pivot axially down. This pivoting feature allows the discrete retainer 10 to be prepackaged or initially secured by the healthcare provider to one of the tubular connectors at one of the open collars as shown in FIG. 1. After the second fluid conduit has been connected in fluid communication to the first fluid conduit, the second collar of the discrete retainer can be utilized to axially secure the second connector relative to the first connector. As shown in FIG. 2, the second collar 28 is rotated about the first pivotable joints 40 and 42 so that the opening 30 of the second collar 28 can easily engage the second tubular connector. The collar 28 pivots on its own pivotable joints 44 and 46 to radially (perpendicularly) engage by a snap fit to the tubular connector.

As best seen in FIG. 3, at least one or both of the pairs of pivotable joints 40 and 42 and/or 44 and 46 are offset (distance B and/or distance A respectively) from the axial center of the respective collars. The offset joint pulls the mouth portion of the open collars together and increases the radial retaining force of the retainer collars 24 and 26 on the tubular connectors when the connectors are being axially pulled apart. Thus the open collars become self-locking when the retainer is in axial tension.

Figures 4, 4A:
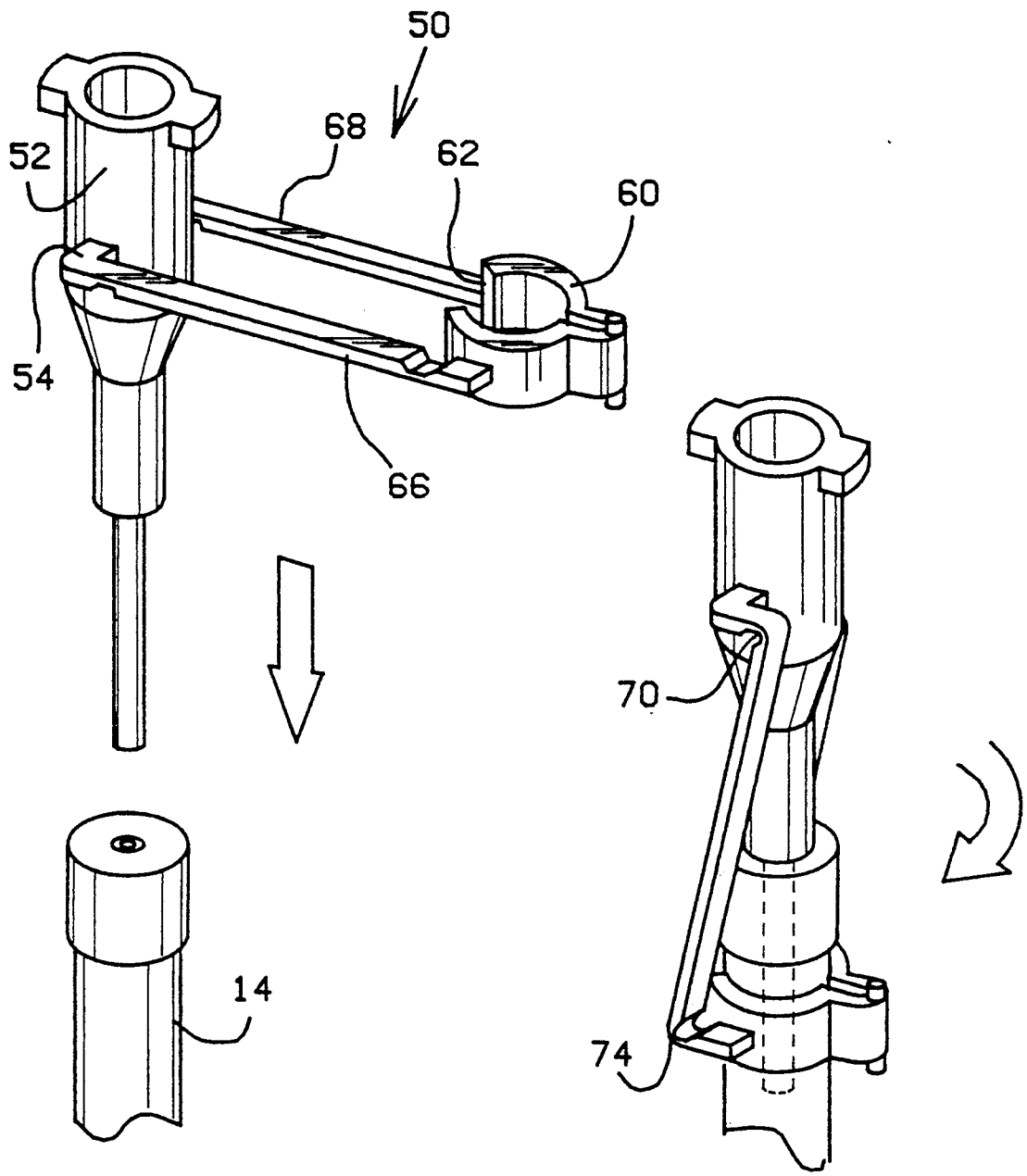
FIG. 4 is an alternative embodiment of the present invention showing a perspective view of a retainer integrally manufactured with one connector and prior to flow connection to a second connector.
FIG. 4A is a perspective view of the integral connector and retainer with the connector portion in flow communication with a second connector and the retainer portion secured to the second connector.
Figure 5:
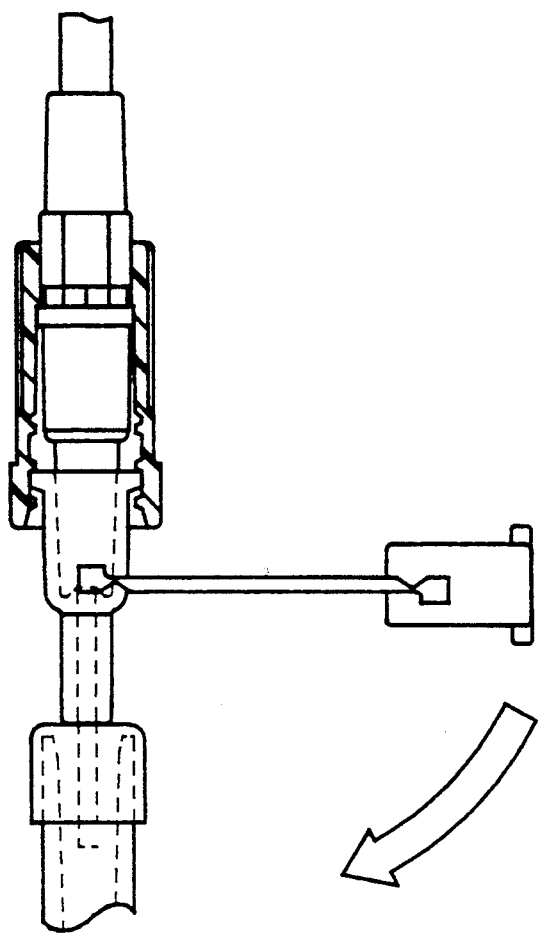
FIG. 5 is a partial cutaway side view of the integral connector and retainer with the connectors in fluid flow connection.
Figure 6:
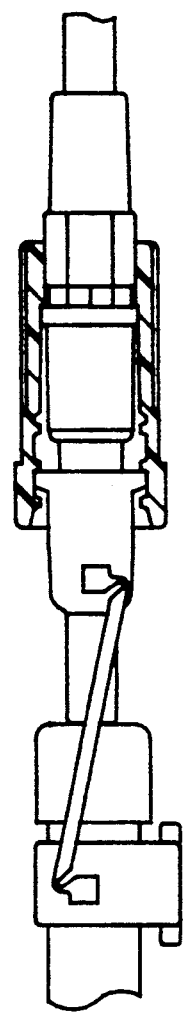
FIG. 6 is a side view of the integral connector and retainer in fluid communication with the retainer fully secured to the second fluid flow connector.
Figure 5A:
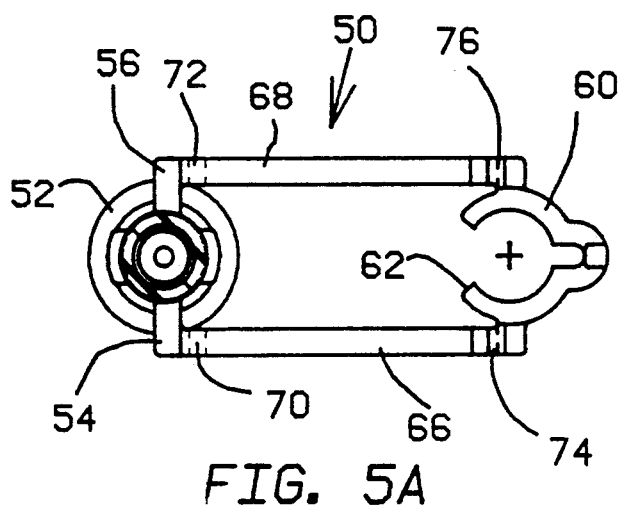
FIG. 5A is a bottom view of FIG. 5.

Turning now to an alternative embodiment shown in FIGS. 4-6, an integral connector and retainer 50 is shown in FIG. 4. The integral connector and retainer includes an axially extending body portion 52. A pair of opposed projections 54 and 56 extend perpendicularly from the axially extending body portion 52 of the integral connector and retainer. The integral retainer and connector further includes an open collar 60 having a flexible opening 62 that is dimensioned so as to be securely and radially attachable by a snap fit to the second tubular connector 14. A pair of parallel straps 66 and 68 connect the opposed projections 54 and 56 to the open collar 60. The straps are connected at a first end to the opposed projections by a pair of axially pivotable joints 70 and 72. The straps are connected at a second end to the open collar 60 by a second pair of axially pivotable joints 74 and 76.

The first and second pair of pivotable joints of the integral connector and retainer 50 pivot in opposite axial directions. Also, at least one and preferably both pair of pivotable joints are offset from the respective axial center of the open collar 60 and/or the axially extending body portion 52. This offset pulls the mouth portion of the open collar together and increases the radial retenting force of the collar on the tubular connector when the connectors are being axially pulled apart. Thus the open collar becomes self-locking when the connectors are in axial tension.

Figure 7:
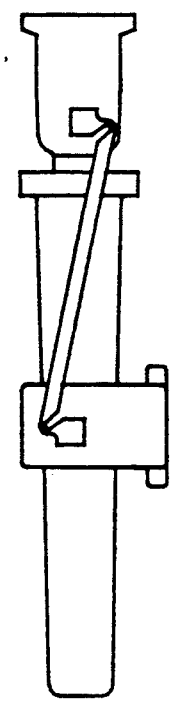
FIG. 7 is a side view of a cannula guard for the integral connector and retainer.

FIG. 7 shows a cannula guard fitted over the blunt cannula portion of the integral cannula and retainer.

In operation, the retainer of the present invention prevents the inadvertent disengagement of intravenous tubing sets. Furthermore, the retainer may be initially placed on one of the connectors for easy engagement with the second tubular connector when the two conduits are in fluid flow communication. The retainer can be easily manipulated with one hand to both engage and disengage the tubular connectors. This facilitates easy disengagement of a connector should disconnection of the intravenous tubing set be necessary.

A further advantage of the retainer is that it can be manufactured by straight pull injection molding. The discrete retainer 10 is molded in the substantially linear configuration shown in FIG. 1A. The integral connector and retainer 50 is molded in the substantially linear configuration shown in FIG. 4. Both of these configurations allows a straight pull plastic injection molding process thus reducing manufacturing complexity.

An additional advantage of the retainer of the present invention is that the unengaged collars tend to return to their initial manufactured configuration when not secured to the tubing connectors. This unengaged orientation perpendicular to the axis of the tubular flow connectors serves two useful purposes. First, it moves the unengaged collar of the retainer out of the way while the connectors are connected in fluid flow communication. Second, the unengaged perpendicular position alerts the healthcare provider that the retainer has not been fully secured to both connectors and inadvertent disengagement of the connectors is possible.

While several embodiments of the invention have been described, modifications within the scope of the present invention will be readily apparent to one of ordinary skill in the art. For example, the retainer of the present invention may be used with any of the known intravenous fluid flow connectors, such as luer connectors and sharp needles and reseals, although the connectors shown in the disclosed embodiments are limited to blunt cannula and pre-pierced reseals. All such modifications are intended to be covered by the scope of the accompanying claims.

What is claimed is:

1. A retainer used in combination with first and second tubular fluid flow connectors, the first connector having a first increased diameter radial shoulder, the first connector axially connected in fluid flow communication with the second tubular fluid flow connector, the second connector having a second increased diameter radial shoulder, the retainer comprising:
- a first open collar having a first flexible opening so as to be radially attachable to the first tubular connector adjacent to the first radial shoulder;
- a second open collar having a second flexible opening so as to be radially attachable to the second tubular connector adjacent to the second radial shoulder; and
- a pair of parallel straps connecting the first collar to the second collar, the pair of straps connected at a first end by a first pair of axially pivotable joints to the first collar and connected at a second end by a second pair of axially pivotable joints to the second collar.

2. The retainer of claim 1 wherein the first and second pair of pivotable joints pivot in opposite axial directions.

3. The retainer of claim 1 wherein at least one of the first and second pair of pivotable joints is offset from the axial center of one of the first and second collars.

4. The retainer of claim 1 wherein the first and second open collars have openings that are dimensioned so as to attach to the respective tubular connectors with a snap fit.

* * * * *